(12) United States Patent
Farrell et al.

(10) Patent No.: US 11,590,264 B2
(45) Date of Patent: Feb. 28, 2023

(54) METHODS OF SELECTIVELY MODIFYING THE FLEXIBILITY OF MEDICAL TUBES

(71) Applicant: Hollister Incorporated, Libertyville, IL (US)

(72) Inventors: David J. Farrell, Ballina (IE); Padraig M. O'Flynn, Ballina (IE); John P. O'Mahony, Ardnacrusha (IE); Richard Meaney, Westport (IE); John T. Clarke, Galway (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 16/325,538

(22) PCT Filed: Aug. 29, 2017

(86) PCT No.: PCT/US2017/049022
§ 371 (c)(1),
(2) Date: Feb. 14, 2019

(87) PCT Pub. No.: WO2018/044839
PCT Pub. Date: Mar. 8, 2018

(65) Prior Publication Data
US 2019/0201589 A1 Jul. 4, 2019

Related U.S. Application Data

(60) Provisional application No. 62/380,813, filed on Aug. 29, 2016.

(51) Int. Cl.
*A61K 9/00* (2006.01)
*A61L 29/14* (2006.01)

(52) U.S. Cl.
CPC .......... *A61L 29/141* (2013.01); *A61L 29/143* (2013.01); *A61L 2400/10* (2013.01); *A61L 2400/18* (2013.01)

(58) Field of Classification Search
CPC .................................................. A61L 29/141
See application file for complete search history.

(56) References Cited

U.S. PATENT DOCUMENTS

| | | | |
|---|---|---|---|
| 3,556,874 A | 8/1968 | Shepherd |
| 3,524,447 A | 8/1970 | Evans et al. |
| 3,566,874 A | 3/1971 | Shepherd |
| 3,924,634 A | 12/1975 | Taylor |
| 4,961,954 A | 10/1990 | Goldberg et al. |
| 5,484,565 A | 1/1996 | Larsen et al. |
| 5,489,269 A | 2/1996 | Aldrich |

(Continued)

FOREIGN PATENT DOCUMENTS

| | | |
|---|---|---|
| EP | 0729766 A1 | 9/1996 |
| EP | 0514913 B1 | 3/1997 |

(Continued)

OTHER PUBLICATIONS

International Search Report and Written Opinion dated Nov. 23, 2017 for International Application No. PCT/US2017/049022.

(Continued)

*Primary Examiner* — Paul W Dickinson
(74) *Attorney, Agent, or Firm* — Cook Alex Ltd.

(57) ABSTRACT

Methods of varying the stiffness of polymeric medical tubes.

18 Claims, 1 Drawing Sheet

(56) References Cited

U.S. PATENT DOCUMENTS

| | | |
|---|---|---|
| 5,922,443 A | 7/1999 | Larsen et al. |
| 6,146,688 A | 11/2000 | Morgan |
| 6,591,472 B1 | 7/2003 | Noone et al. |
| 6,875,197 B1* | 4/2005 | Simhambhatla ........ A61L 29/06 604/103.06 |
| 7,264,609 B2 | 9/2007 | Hamid |
| 7,717,902 B2 | 5/2010 | Sauer |
| 8,251,976 B2 | 8/2012 | Zhou |
| 8,361,057 B2 | 1/2013 | Tanghoej |
| 8,734,427 B2 | 5/2014 | Triel et al. |
| 8,795,573 B2 | 8/2014 | Bracken |
| 9,561,346 B2 | 2/2017 | Zvulonl |
| 9,789,284 B2 | 10/2017 | Nickel |
| 9,913,960 B2 | 3/2018 | Blanchard |
| 9,937,318 B2 | 4/2018 | Bonneau |
| 2004/0002729 A1 | 1/2004 | Zamore |
| 2005/0033237 A1 | 2/2005 | Fentress |
| 2006/0095019 A1 | 5/2006 | Dikeman |
| 2007/0048349 A1 | 3/2007 | Salamone et al. |
| 2007/0082393 A1 | 4/2007 | Lodhi et al. |
| 2010/0100009 A1 | 4/2010 | Nielsen et al. |
| 2011/0213318 A1 | 9/2011 | Schertiger |
| 2015/0018431 A1 | 1/2015 | Zeng |
| 2015/0196690 A1 | 7/2015 | Stankus et al. |
| 2015/0297863 A1 | 10/2015 | Hannon |
| 2016/0184551 A1 | 6/2016 | Nyman |
| 2017/0368232 A1* | 12/2017 | Montes de Oca .... A61L 29/041 |
| 2018/0001055 A1 | 1/2018 | Utas |

FOREIGN PATENT DOCUMENTS

| | | | |
|---|---|---|---|
| EP | 1053039 B1 | 12/2005 | |
| EP | 2445565 B1 | 8/2015 | |
| JP | 08164196 A | 6/1996 | |
| WO | WO 1991/007203 A1 | 5/1991 | |
| WO | WO 0033907 A1 | 6/2000 | |
| WO | WO 2005018727 A1 | 3/2005 | |
| WO | WO 2006/031582 A2 | 3/2006 | |
| WO | WO 2006069579 A2 | 7/2006 | |
| WO | WO 2007012050 A2 | 1/2007 | |
| WO | WO 2007027500 A2 | 3/2007 | |
| WO | WO 2010149174 A1 | 12/2010 | |
| WO | WO 2011071627 A1 | 6/2011 | |
| WO | WO-2014077881 A * | 5/2014 | ........ A61M 25/0013 |
| WO | WO 2015/019056 A1 | 2/2015 | |
| WO | WO 2016118569 A1 | 7/2016 | |

OTHER PUBLICATIONS

Examination Report in European Application No. 17764735.1 dated May 5, 2020.

European Office Action dated Feb. 10, 2021 for European Application No. 17764735.1.

* cited by examiner

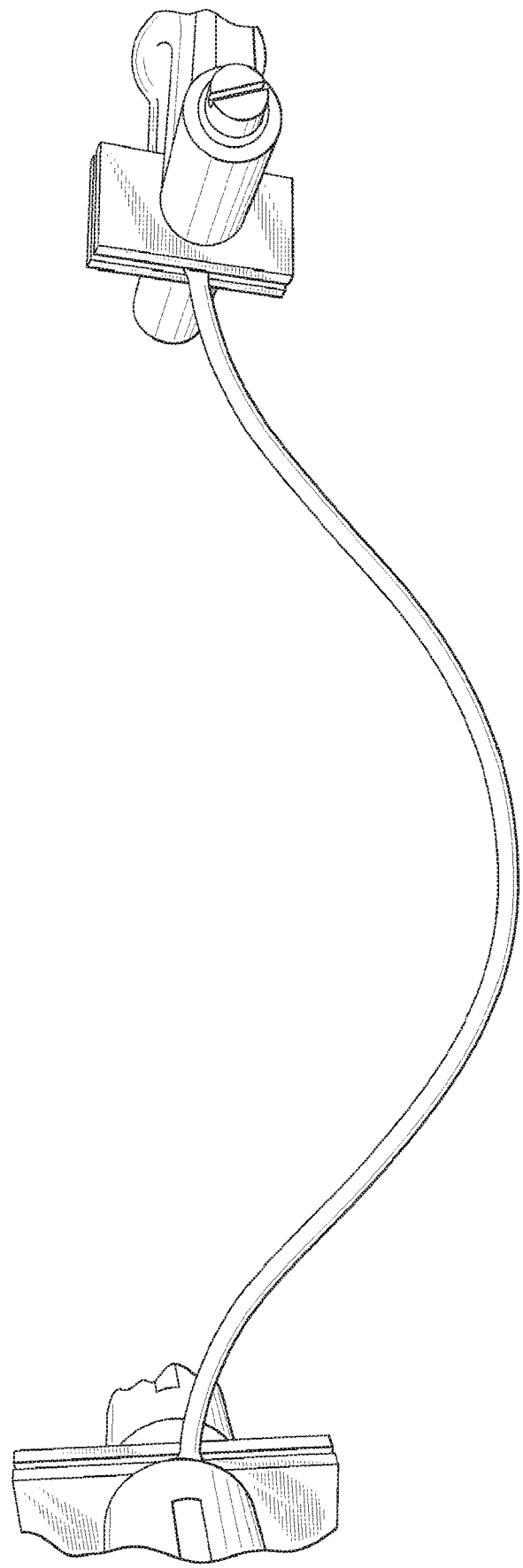

US 11,590,264 B2

METHODS OF SELECTIVELY MODIFYING THE FLEXIBILITY OF MEDICAL TUBES

The present application is the U.S. National Stage Application of PCT Application No. PCT/US2017/049022, filed Aug. 29, 2017, which claims the benefit of and priority to U.S. Provisional Patent Application No. 62/380,813, filed Aug. 29, 2016, the disclosures of which are incorporated herein by reference.

TECHNICAL FIELD

The present disclosure generally relates to methods of selectively modifying the durometer of medical tubes, and more particularly, to methods of selectively modifying the stiffness of urinary catheter tubes so that the tubes include sections of differing flexibility along the length of the catheter tubes.

BACKGROUND

Catheters are used to treat several different types of medical conditions and typically include an elongated shaft or tube that is inserted into and through a passageway or lumen of the body. Catheters, and in particular intermittent urinary catheters, are commonly used by those who suffer from various abnormalities of the urinary system, such as urinary incontinence. With the advent of intermittent urinary catheters, individuals with urinary system abnormalities can self-insert and self-remove intermittent catheters several times a day to drain the bladder.

In some applications, it may be desirable for a catheter to vary in flexibility along the catheter tube so that the catheter includes the benefits of both a stiff and soft catheter in a single catheter device. That is, it may be desirable for one or more sections of the catheter tube to be more pliable or flexible than other sections. For example, because of the natural contours of the urethra, it may be desirable for a urinary catheter tube to have a softer, more flexible proximal insertion end portion that enables easier insertion of the catheter tube into the urethra. The more flexible proximal end portion also may aid in the navigation of the catheter tube through the natural contours of the urinary system. A more flexible proximal end portion may be especially beneficial to male users wherein the more flexible proximal end portion may aid in advancement and navigation through the curved path of the urethra of a male user. It may also be desirable for the catheter to have a stiffer rear section that facilitates the user's handing and maneuverability of the catheter.

Therefore, there is a need for catheters having varying flexibility and methods for making the same.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method of modifying a polymeric medical tube includes contacting at least a section of the polymeric medical tube with an anti-plasticizer, such as a polymerizable monomer. The polymerizable monomer being absorbed into the section of the polymeric medical tube. The polymerizable monomer absorbed in the section of the polymeric medical tube is polymerized, thereby resulting in an anti-plasticizer effect, i.e., increasing the stiffness/reducing the plasticity of the section of the polymeric medical tube.

In another aspect, a method of modifying a polymeric medical tube includes contacting at least a section of the polymeric medical tube with a polymerizable monomer, the polymerizable monomer being absorbed into the section of the polymeric medical tube, thereby increasing the flexibility of the section of the polymeric medical tube.

BRIEF DESCRIPTION OF THE DRAWINGS

FIG. 1 is a picture showing the apparatus for measuring the critical buckling force of a tube.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to medical devices that include shafts or tubes that may be inserted into and advanced within a lumen of a body, such as a urethra, esophagus, or fallopian tube. Such medical devices include urinary catheters, endovascular catheters, endoscopes, exploratory and biopsy devices, etc. While some of the embodiments set forth below may be described in the context of urinary catheters, the disclosure is not limited to such and the features disclosed herein may be applicable to any medical tubing that is inserted into a body lumen.

When used in the context of a tube that is inserted into the body of the user, such as a urinary catheter tube, the term "proximal" is used to refer to an end or portion of a catheter tube that is closer in proximity to the user's body and/or enters the user's body. The term "distal" is used to refer to an end or portion that is opposite the proximal end or portion and is typically further away from the user's body.

The medical tubes disclosed herein may vary in stiffness/flexibility along the length of the tube. Depending on the application, the medical tube may have a proximal end portion that is relatively more flexible or pliable than a relatively stiffer distal end portion. In other applications, the medical tube may have a distal end potion that is relatively more flexible or pliable than a relatively stiffer proximal end portion. In yet other applications, the medical tube may include alternating sections of relative flexibility and stiffness, e.g. a relatively flexible section adjacent to a relatively stiffer section that is adjacent to a relatively flexible section, etc. In medical tubes that include multiple flexible and/or stiff sections, the relatively more flexible sections may differ in flexibility relative to each other. Similarly, the relatively stiffer sections may differ in stiffness relative to each other.

In one application, a urinary catheter may include a catheter tube or shaft that has a proximal end portion and a distal end portion. The proximal end portion of catheter tube may include an insertion tip and eyelets or drainage openings for draining urine from the bladder. The distal end portion of the catheter tube may have a drainage member, such as a funnel, associated therewith. The drainage member may be integral with the catheter tube or may be attached to the catheter tube. The catheter tube has a lumen extending therethrough for the passage of urine from the eyelets to the drainage member. The drainage member may be a free end that the user can extend to a waste receptacle such as a toilet or the drainage member may be connected to a collection bag. Furthermore, the tubes may also be lubricous so as to ease advancement and withdrawal of the tube into and from the body lumen. The catheter tube may include a lubricous hydrophilic coating disposed on the outer surface of the catheter tube or the tube may be lubricated with a gel-type lubricant that is applied to the outer surface of the catheter tube.

In one embodiment of a catheter tube, the catheter tube may have a more flexible proximal end portion that facilitates insertion and navigation through the urethra and a stiffer distal end portion that facilitates handling, maneuverability and/or advancement of the catheter tube as the user advances/pushes the catheter tube into the urethra, by for example gripping and pushing the distal end portion of the catheter. Optionally, a section of the distal end portion of the catheter tube adjacent to the drainage member may also be more flexible than the rest of the distal end portion such that it may be easier to bend such section to direct the drainage member to a waste receptacle or so that the urine collection bag may be moved into a convenient location by the user. Furthermore, the proximal insertion tip of the catheter tube may be more rigid that the rest of the proximal end portion to aid in insertion of the tip into the urethra.

The methods disclosed herein for making catheter tubes of varying flexibility may include treatments with polymerizable monomers that soften selective sections of the medical tube and treatments with polymerizable monomers that harden selective sections of the medical tube.

The catheter tubes may be made from any suitable polymeric material such as polyvinyl chloride (PVC), thermoplastic polyurethane (TPU), thermoplastic elastomer (TPE), thermoplastic polyolefin (TPO), PEBAX etc. In some embodiments, the polymeric materials of the catheter, prior to being subjected to the methods disclosed herein, may include a plasticizer. For example, the material of the catheter may include plasticized PVC, TPU, and/or TPE, etc. In one embodiment, the polymeric material is PVC plasticized with trioctyl trimellitate (TOTM).

The polymerizable monomers may be those that are capable of being absorbed into or capable of infiltrating the polymeric material of the catheter tube. The polymerizable monomers may be, for example, vinyl ethers and/or acrylates. The polymerizable monomers may include Tricyclo [$5.2.1.0^{2,6}$]decanedimethanol diacrylate (TCDDM-DA), Trimethylolpropane ethoxylate triacrylate (TMPE-TA), Trimethylolpropane trimethacrylate (TMP-TMA), Trimethylolpropane triacrylate (TMP-TA), Neopentyl glycol propoxylate (1 PO/OH) diacrylate (NPGP-DA), 1,6-Hexanediol ethoxylate diacrylate (HDE-DA), Hydroxypivalyl hydroxypivalate bis[6-(acryloyloxy)hexanoate] (HPHPBAH-DA), Tri(ethylene glycol) divinyl ether (TEG-DVE), Tetrahydrofurfuryl acrylate (THF-A), Tetrahydrofurfuryl methacrylate (THF-MA), Limonene, Tetrahydrofuran (THF), 2-Methyltetrahydrofuran (2-MeTHF) or mixtures thereof. In one embodiment, a mixture of monomers may include Limonene and acrylates. In another embodiment, the mixture of monomers may be THF and vinyl ethers.

Methods of Increasing Flexibility/Reducing Stiffness of Catheter Tubes

The flexibility of selected sections of a catheter tube may be modified by selectively treating sections of the catheter tube to soften the polymeric material of the tube. In one method of modifying the catheter tube, at least a section of the catheter tube may be contacted with one or more of the above-mentioned polymerizable monomers. The section of the catheter tube may be placed in contact with a single type of polymerizable monomer or a mixture including multiple polymerizable monomers. In other embodiments, the section of the tube may be placed in successive contact with multiple polymerizable monomers. The section(s) of the catheter tube may be placed in contact with the polymerizable monomer by any suitable manner including but not limited to spraying, dipping, painting, and/or application by aerosol and inkjet. While in contact with the polymerizable monomer, the monomers infiltrate or are absorbed into the polymeric material of the section(s) of the catheter tube which results in a softening of the polymeric material and an increase in the flexibility of the section(s) of the catheter tube.

The amount of polymerizable monomer absorbed into the polymeric material may depend on, among other conditions, time period of contact of the polymerizable monomer with the polymeric material of the catheter tube, the temperature and/or pressure of the conditions under which contact takes place and/or if the polymeric material has previously been plasticized (i.e., includes a plasticizer). Depending on the polymerizable monomer, the polymeric material of the catheter tube and/or the desired flexibility to be achieved by the treatment, the section(s) of the catheter tube may be placed in contact with the polymerizable monomer for a selected time period at a selected temperature and/or pressure. The time period of contact with the polymerizable monomer, the temperature and/or pressure of the conditions under which the monomer is contacted with the catheter tube and the initial amount of plasticizer in the polymeric material prior to treatment may be adjusted to produce a desired flexibility of the section(s) of the catheter tube. One manner of determining the amount of polymerizable monomer that has been absorbed by the catheter tuber is to compare the original/pre-treated weight of the catheter with the weight of the catheter after treatment. In some embodiments, catheter tubes, or sections thereof, that have absorbed the polymerizable monomer may weigh between about 100.5% and about 120% of the original weight of the catheter. Preferably, treated catheter tubes, or sections thereof, weigh between 101% and 108% of the original weight of the catheters.

After the catheter tube has been in contact with the polymerizable monomer, the catheter tube may be removed from contact with the polymerizable monomer and the surface of the catheter tube may be wiped off and/or rinsed to remove excess polymerizable monomer from the surface of the tube. A hydrophilic coating may then be applied to the catheter tube or the catheter tube may be used with a gel-type lubricant.

In one method of modifying the flexibility of a catheter tube, the proximal insertion end portion of a relatively stiff catheter tube is placed in contact with the polymerizable monomer. The catheter tube may have, for example, a Shore A hardness of between 85 A and 95 A. A section of the catheter tube (such as a length of the tube) that may be between about 5% to about 50% of the tube may be placed in contact with the polymerizable monomer. The section may extend distally from the proximal insertion tip. For example, male catheters typically have a length about 20 cm and 40 cm. In a male catheter having a length of 20 cm, a section of about 1 cm to about 10 cm of the proximal end portion may be contacted by the polymerizable monomer. In male catheters having a length of about 40 cm, a section of about 2 cm to about 20 cm of the proximal end portion may be contacted by the polymerizable monomer. Optionally, the proximal insertion tip of the catheter tube may not be placed into contact with the polymerizable monomer so that the proximal insertion tip retains its stiffness while the rest of the proximal end portion, which is placed in contact with the polymerizable monomer, is made relatively flexible. Additionally, a section of the distal end portion adjacent to the drainage member may also be brought into contact with the polymerizable monomer to render this section more flexible so that the user may bend and direct the drainage member during catheterization.

The section(s) of the catheter to be made softer may be brought into contact with the polymerizable monomer in any of the above-mentioned manners or any other suitable manner. For example, the section to be placed into contact with the polymerizable monomer may be dipped into or immersed within the polymerizable monomer while the other section(s) of the catheter tube do not come into contact with the polymerizable monomer.

Optionally, the sections of the catheter tube that are not to be treated with the polymerizable monomer may be masked or protected to substantially prevent ingress of the polymerizable monomer into the masked or protected sections. The mask may be a polymer coating of one or more of polyvinylpyrrolidone (PVP), polyethylene oxide (PEO), polyvinyl alcohol (PVOH), hydroxypropyl methylcellulose (HPMC), hydroxyethyl methylcellulose (NEMC), Chitosan, Cellulose Acetate or any other suitable mask. The mask may be applied to the section(s) of the catheter by applying a masking solution to the section(s) to be protected. The solution may include any of the immediately mentioned polymers and a solvent, such as water, methanol, ethanol or isopropanol or mixtures thereof. In one embodiment, the masking solution may be PVP and ethanol. For example, the PVP may be in an amount between about 2.5 wt % and about 10 wt % and the ethanol may be between about 90 wt % and about 97.5 wt %. The mask may be applied in any suitable manner, such as dip coating or spraying. Additionally, the mask could be graduated or include a gradient/gradual transition from a thicker mask to a thinner mask wherein the thinner mask allows for some of the monomer to be absorbed into the catheter. Thus, the graduated mask will result in a gradient of absorbed monomer in the tube, and when the thinner section of the mask is adjacent the transition between the relatively stiffer and relatively softer sections of the tube, it will provide a gradual transition between the sections. This may assist in the preventing of kinking or buckling of the catheter during use. In one method, a graduated mask may be achieved in a dip coating process wherein there is a gradual withdrawal speed, differential in dip time, etc. After the masking solution is applied to the sections of the catheter to be protected, the solution is then dried to form a mask on such sections. For example, the mask may be applied to a section of the distal end portion of the catheter. In other embodiments, the mask may be applied to alternating sections of the catheter. In one embodiment, the proximal insertion tip is masked while a section of the remaining proximal end portion is unmasked and a section of the distal end portion is masked, while another section of the distal end portion adjacent the drainage member is unmasked. Masking the catheter in this manner will result in a catheter tube that has a relatively stiffer proximal insertion tip that is adjacent to a relatively flexible proximal end section which is adjacent to a relatively stiffer distal end section which is adjacent to a relatively flexible distal end section which is adjacent to the drainage member.

The entire catheter tube may then be dipped or immersed into the polymerizable monomer wherein the polymerizable monomer is absorbed into the unmasked sections and the mask substantially prevents polymerizable monomer from infiltrating the masked sections. After a desired amount of polymerizable monomer is absorbed into the unmasked sections, the catheter is removed from the polymerizable monomer and then rinsed and/or wiped to remove any excess polymerizable monomer. The mask is removed from the surface of the catheter tube by rinsing. Optionally, the catheter tube may be then coated with a hydrophilic coating or may be used with a gel lubricant. The treated catheter tube now includes a varying flexibility along the length of the catheter tube.

Methods of Hardening/Stiffening Selective Sections of a Catheter Tube

The flexibility of selected sections of a catheter tube may be modified by selectively treating sections of the catheter tube with an anti-plasticizer, such as a polymerizable monomer, to harden or stiffen the polymeric material of the tube. In one embodiment, an anti-plasticizing composition includes a mixture of a polymerizable monomer(s) and a suitable amount of an initiator.

In one method of modifying the catheter tube, at least a section of the catheter tube may be contacted with an anti-plasticizing composition including a mixture of one or more of the above-mentioned polymerizable monomers and an amount of an initiator. The section(s) of the catheter tube may be placed in contact with the mixture of the polymerizable monomer(s) and initiator by any of the above-described manners or by any other suitable manner. While in contact with the mixture, the monomer(s) and initiator infiltrate or are absorbed into the polymeric material of the catheter tube. The sections of the catheter tube are removed from contact with the mixture and the polymerizable monomers that have been absorbed into the polymeric material of the catheter tube are then polymerized, which results in an anti-plasticizing effect, i.e., a hardening of the polymeric material and an increase in the stiffness of the section(s) of the catheter tube. Polymerization may be homopolymerization or copolymerization, depending on the type of monomers present in the mixture.

Similar to as described above, the amount of the mixture of polymerizable monomer(s) and initiator absorbed into the polymeric material may depend on, among other conditions, the time period that the mixture is in contact with the polymeric material of the catheter tube, the temperature and/or pressure of the conditions under which contact takes place and/or whether the polymeric material of the catheter has been previously plasticized. The time period of contact with the mixture, the temperature and/or pressure of the conditions under which the mixture is contacted with the catheter tube and the initial amount of plasticizer in the polymeric material prior to treatment may be adjusted to result in a desired amount of polymerizable monomer being absorbed into the section(s) of the catheter tube. One manner of determining the amount of mixture absorbed by the catheter is to compare the original/pre-treated weight of the catheter with the weight of the catheter after exposure to the mixture. In some embodiments, the catheter tubes, or sections thereof, having absorbed the mixture of polymerizable monomer and initiator may weigh between about 100.5% and about 120% of the original weight of the catheter shaft. Preferably, catheter shafts, or sections thereof, after exposure to the mixture weigh between 101% and 108% of the original weight of the catheter shafts.

After the catheter tube has been in contact with the polymerizable monomer/initiator mixture and a desired amount of the mixture has been absorbed into the polymeric material of the section(s) of the catheter tube, the section(s) of the catheter tube may be removed from contact with the polymerizable monomer/initiator mixture and the surface of the catheter tube may be wiped off and/or rinsed to remove excess polymerizable monomer/initiator mixture. The polymerizable monomer within the polymeric material of the section(s) of the catheter tube may then be polymerized which hardens the polymeric material of the catheter.

In one embodiment of the method, the initiators may include acetophenones, benzil and benzoin compounds, benzophenone, thioxanthones, latent cationic initiators e.g. diphenyliodonium, triphenisulphonium and other salts of non-nucleophilic anions, peroxides, and redox couples such as cumene hydroperoxide/acetyl phenyl hydrazine or Fenton's reagent ($Fe^{II}/H_2O_2$) systems. The initiator may be about 0.05 wt % and about 5.0 wt % of the mixture. After the catheter has been removed from being in contact with the mixture and a desired amount of polymerizable monomer and initiator have been absorbed into the polymeric material, the initiator may be activated to polymerize the monomer. The initiator may be a radiation initiator that is activated by radiation, such as UV light, E Beam, etc. When the initiator is a photo-initiator, the catheter may be exposed to UV light to polymerize the monomer within the polymeric material of the catheter tube. In another embodiment, the catheter may be exposed to E Beam or any other practical radiation source to polymerize the monomer. This may be useful when a catheter is made from an opaque material.

Optionally, when the method includes forming a hydrophilic coating on the catheter and the forming of the hydrophilic coating includes curing by exposure to UV light, polymerizing the monomer and curing the hydrophilic coating may be accomplished concomitantly by exposure to UV light. Thus, polymerization of the monomer and curing of the hydrophilic coating can be consolidated into a single operation.

In an alternative embodiment of the method of anti-plasticizing the catheter, monomer(s), without any initiator, may be absorbed into the material of the catheter by exposure of the catheter to the monomer(s) in any of the above-described manners. Similar to as described above, the conditions of exposure of the monomer(s) to the catheter can be adjusted so that a desired amount of monomer is absorbed. The catheter or the portion(s) thereof having absorbed the monomer(s) may then be exposed to E Beam radiation or any other suitable radiation to initiate polymerization of the monomer(s).

In one method of modifying the tube, the entire tube may be placed in contact with the mixture of monomer(s) and initiator so that the mixture is absorbed into the entire tube. In another method of modifying the flexibility of a catheter tube, a section of the distal end portion of a relatively flexible catheter tube is placed in contact with a mixture of polymerizable monomer and initiator.

The catheter tube may have, for example, a Shore A hardness of between about 60 A and about 87 A. The section of the catheter tube (such as a length of the tube) that is placed in contact with the mixture may be a section that is about 10% to about 70% of the tube, and preferable about 10% to about 50%. For example, male catheters typically have a length about 20 cm and 40 cm. In a male catheter having a length of 20 cm, a section of about 2 cm to about 14 cm extending proximally from the distal end portion may be contacted by the mixture. In male catheters having a length of about 40 cm, a section of about 4 cm to about 24 cm extending proximally from the distal end portion may be contacted by the mixture. Optionally, a section of the distal end portion near or adjacent to the drainage member may not be placed into contact with the polymerizable mixture so that this section retains its flexibility while the section of the distal end portion which is contacted by the polymerizable mixture is made relatively stiffer. Maintaining the flexibility of a section near or adjacent to the drainage member may aid in allowing the user to bend and direct the drainage member during catheterization.

Similar to as discussed above, the portions of the catheter tube that are not to be treated with the polymerizable monomer may be masked or protected to substantially prevent ingress of the mixture of polymerizable monomer and initiator into the masked or protected sections. The mask may be any of the polymer coatings discussed above or any other suitable mask. The mask may be applied to the section(s) of the catheter by applying a masking solution to those section(s) to be protected. In one embodiment, the masking solution may be PVP and ethanol. Furthermore, as discussed above, the mask may be graduated. After the masking solution is applied to the sections of the catheter tube to be protected, the solution may then be dried to form a mask on such sections. For example, the mask may be applied to the proximal end portion of the catheter. In other embodiments, the mask may be applied to alternating section of the catheter. In one embodiment, the proximal insertion tip is left unmasked while the remaining proximal end portion is masked and the distal end portion is unmasked, except that a section of the distal end portion adjacent the drainage member is masked. Masking the catheter in this manner will result in a catheter tube that has a relatively stiffer proximal insertion tip adjacent a relatively flexible proximal end section, adjacent a relatively stiffer distal end section which is adjacent to a relatively flexible distal end section adjacent the drainage member.

The entire catheter tube may then be dipped or immersed into the mixture of polymerizable monomer and initiator wherein the polymerizable monomer and initiator are absorbed into the unmasked sections and the mask substantially prevents polymerizable monomer and initiator from infiltrating the masked sections. After a desired amount of the mixture is absorbed into the unmasked sections, the catheter is removed from the mixture and then rinsed to remove the excess polymerizable monomer and initiator. The polymerizable monomer absorbed into the polymeric material of the catheter shaft may then be polymerized which results in a hardening of the catheter shaft, producing a stiffer catheter. The mask may be washed from the surface of the catheter tube before or after polymerization. Optionally, the catheter tube may be then coated with a hydrophilic coating or may be used with a gel lubricant. When the catheter includes a hydrophilic coating that requires exposure to UV light to "dry" or cure the coating, the exposure to the UV light could also serve to cure the polymerizable monomer composition absorbed into the catheter. The treated catheter tube now includes a varying flexibility along the length of the catheter tube.

In an alternative embodiment, a reel-to-reel process may be used to treat long lengths of tubing that may be cut to length after treatment. For example, alternating regions of tubing may be systematically dipped and cured in-line in a reel-to-reel process. In such a process, the tubing would be unwound from an initial reel and regions of the tubing would be systematically dipped into the monomer or monomer/initiator mixture and then cured. The tubing would then be rewound onto a second reel. The tubing could then be cut to length from the second reel.

EXAMPLES

Example 1

PVC catheter tubes having a Shore A hardness of 92 A were weighed. The tubes were immersed at room temperature for nine minutes in one of the below listed polymerizable monomers. The catheter tubes were removed from the respective polymerizable monomers and then rinsed with ethanol to remove excess polymerizable monomer from the surface of the catheter tube. The tubes were then reweighed and the percentage of weight gain from absorbing the respective polymerizable monomer over the original weight was calculated. The Shore A hardness was then measured using a Shore® Instruments Shore A hardness gauge. The results are shown in Table 1.

TABLE 1

| Sample | Polymerizable Monomer | Percent Weight Gain | Shore A Hardness |
|---|---|---|---|
| 1 | None | 0% | 92 |
| 2 | Limonene | 1.8% | 90 |
| 3 | Trimethylolpropane ethoxylate triacrylate (TMPE-TA) | 1.0% | 89 |
| 4 | Trimethylolpropane trimethacrylate (TMP-TMA) | 0.6% | 89 |
| 5 | Neopentyl glycol propoxylate (1 PO/OH) diacrylate (NPGP-DA) | 1.5% | 88 |
| 6 | 1,6-Hexanediol ethoxylate diacrylate (HDE-DA) | 2.8% | 87 |
| 7 | Hydroxypivalyl hydroxypivalate bis[6-(acryloyloxy)hexanoate] | 4.8% | 87 |
| 8 | Tri(ethylene glycol) divinyl ether (TEG-DVE) | 4.5% | 83 |
| 9 | Tetrahydrofurfuryl methacrylate (THF-MA) | 16.0% | 75 |
| 10 | Tetrahydrofuran (THF) | 14.9% | 72 |
| 11 | Tetrahydrofurfuryl acrylate (THF-A) | 20.2% | 69 |
| 12 | 2-Methyltetrahydrofuran (2-MeTHF) | 16.4% | 67 |

Example 2

PVC catheters having a Shore A hardness of 92 A were weighed and then immersed in tetrahydrofurfuryl methacrylate (THF-MA) at room temperature. At the each of the below time intervals, a catheter was removed from the THF-MA and rinsed with ethanol to remove excess THF-MA from the surface of the catheter. The catheter was weighed and the Shore A hardness of the catheter was measured using a Shore® Instruments hand held Shore A hardness gauge. Table 2 shows the amount of THF-MA absorbed by the catheter tube and the softening of the catheter tube at each time interval.

TABLE 2

| Time (s) | Percent Weight Gain | Shore A Hardness |
|---|---|---|
| 0 | 0.0% | 92 |
| 10 | 1.1% | 91 |
| 30 | 1.9% | 90 |
| 60 | 3.6% | 88 |
| 90 | 5.3% | 87 |
| 120 | 7.2% | 85 |

TABLE 2-continued

| Time (s) | Percent Weight Gain | Shore A Hardness |
|---|---|---|
| 240 | 9.1% | 84 |
| 540 | 20.2% | 69 |

Example 3

A PVC catheter having a Shore A hardness of 92 A was immersed in tetrahydrofurfuryl methacrylate (THF-MA) at room temperature for 120 seconds. The catheter tube was removed from THF-MA and the Shore A hardness was measured by a Shore® Instruments hand held Shore A hardness gauge. The catheter tube was stored at 40° C. for seven days to simulate accelerated aging. The Shore A hardness of the catheter tube was also measured on days 2, 5 and 7. The results are shown in Table 3 below.

TABLE 3

| Day | Shore A Hardness |
|---|---|
| 1 | 83 |
| 2 | 81 |
| 5 | 79 |
| 7 | 80 |

Example 4

The proximal end portion (~15 cm) of a 40 cm PVC catheter tube having a Shore A hardness of 82 A was vertically dipped into a masking solution that included 10 wt % PVP K90 in 90 wt % Ethanol. The coated proximal end portion was allowed to air dry until dry to the touch to form a mask on the outer surface of the proximal end portion. After the coated proximal end portion was dried, the full length of the catheter tube was dipped into a mixture including 99 wt % of polymerizable solution of tetrahydrofurfuryl methacrylate (THF-MA) monomer and 1 wt % of the photoinitiator Irgacure 2954. The catheter was immersed for 120 seconds and then removed and rinsed in ethanol to remove any excess THF-MA solution from the catheter tube surface. The mask remained in place during this rinsing. The masked portion was then rinsed in running cold water to remove the mask. The full catheter was then rinsed in ethanol to accelerate drying.

The catheter was then coated with a UV curable hydrophilic coating. The hydrophilic coating was formed from a base coat layer and a top coat layer. The base coat and top coat solutions were prepared and applied as indicated below.

The formulation of the base coat composition included the following components:

| Base Coat | |
|---|---|
| Component | Amount (w/w) |
| Methanol | 97.98% (w/w) |
| PVP K90 (Ashland) | 1.61% (w/w) |
| Irgacure 2959 (BASF) | 0.01% (w/w) |
| PEG400DA (SR344, Sartomer, inhibitor removed) | 0.40% (w/w) |

The base coat solution was prepared by slowly adding PVP to methanol while mixing until the PVP was dissolved.

PEG400DA and Irgacure 2959 were then added and allowed to fully dissolve while the composition was stirred.

The formulation of the top coat solution included the following components:

Top Coat

| Component | Amount (w/w) |
|---|---|
| Ethanol (absolute) (Lennox) | 78.99% (w/w) |
| De-ionized water (Lennox) | 14.00% (w/w) |
| PVP K90 (Ashland) | 5.95% (w/w) |
| BHT-A (Sigma Aldrich) | 0.01% (w/w) |
| PEG400DA (SR344, Sartomer, inhibitor removed) | 0.30% (w/w) |
| Glycerol | 0.74% (w/w) |
| Benzophenone | 0.01% (w/w) |

The top coat composition was prepared by adding PVP to the ethanol and water and mixing until dissolved. The remaining components (glycerol, PEG400DA, BHT-A, and benzophenone) were then added and allowed to fully dissolve under stirring.

To form the hydrophilic coating on the outer surface of the catheter, the catheter was immersed in the base coat solution for a period of 10 seconds and then withdrawn at a rate of 0.7 cm/sec using a Harland PCX coating machine containing UV lamps. The base coat solution was then cured and dried under UV lamps for 45 seconds to form a base coat layer on the outer surface of the catheter. The catheters were then immersed in the top coat solution for 10 seconds and withdrawn at a rate of 0.5 cm/sec. The top coat solution was then UV cured and dried under UV lamps for 10 minutes to form the top coat layer, resulting in the formation of the hydrophilic coating on the catheter. The UV lamps also polymerized the THF-MA absorbed in the catheter.

After the hydrophilic coating was applied, a physical inspection of the catheter was conducted. The physical inspection revealed that the masked portion of the catheter had remained soft and flexible while the unmasked distal section of the catheter which had been exposed to the mixture of THF-MA and photoinitiator was noticeably more rigid. Further masking compositions of lower concentration (2.5% and 5.0% PVP in ethanol) were also evaluated with similar results observed.

Example 5

The below listed tubes were cut into six samples wherein each sample had a length of 25 mm.

| Material | Shore A Hardness | French Size |
|---|---|---|
| PVC - Plasticized with TOTM (Supplied by Raumedic) | 82A | 14 |
| TPE - No Plasticizer | 82A | 14 |
| TPE Medalist MD 575 - No Plasticizer (Teknor Apex Company) | 78A | 14 |
| TPU - No Plasticizer (Supplied by Lubrizol Pellethane ® 5863-87A TPU) | 87A | 14 |
| TPU - No Plasticizer | 85A | 14 |

The initial mass of each of the six samples of each of the above-listed tubes was measured and then 5 samples of each of the tubes were immersed in THF-MA. A sample of each one of the tubes was removed for the THF-MA at the intervals of 2 minutes, 5 minutes, 20 minutes, 40 minutes and 60 minutes. When a sample was removed, the excess THF-MA was removed from the sample. Then, the mass of the sample was measured and the change of mass was determined. The results of this Example are shown below in Tables 4-8.

TABLE 4

PVC 82A Ch14 - 25 mm Segments

| Dwell time (min) | Initial Mass (g) | final mass (g) | Change in mass (g) | Change in mass % |
|---|---|---|---|---|
| 0 | 0.2804 | 0.2804 | 0.0000 | 0.0 |
| 2 | 0.2736 | 0.3098 | 0.0362 | 13.2 |
| 5 | 0.2798 | 0.3340 | 0.0542 | 19.4 |
| 20 | 0.2781 | 0.3665 | 0.0884 | 31.8 |
| 40 | 0.2765 | 0.3725 | 0.0960 | 34.7 |
| 60 | 0.2772 | 0.4414 | 0.1642 | 59.2 |

TABLE 5

TPE 82A Ch 14 - 25 mm Segments

| Dwell time (min) | Initial Mass (g) | final mass (g) | Change in mass (g) | Change in mass % |
|---|---|---|---|---|
| 0 | 0.2049 | 0.205 | 0.0001 | 0.05 |
| 2 | 0.2055 | 0.2073 | 0.0018 | 0.88 |
| 5 | 0.2127 | 0.2160 | 0.0033 | 1.55 |
| 20 | 0.2121 | 0.2159 | 0.0038 | 1.79 |
| 40 | 0.2173 | 0.2226 | 0.0053 | 2.44 |
| 60 | 0.2127 | 0.2238 | 0.0111 | 5.22 |

TABLE 6

TPE Medalist MD 575 78A Ch 14 - 25 mm Segments

| Dwell time (min) | Initial Mass (g) | final mass (g) | Change in mass (g) | Change in mass % |
|---|---|---|---|---|
| 0 | 0.2054 | 0.205 | 0.0000 | 0.00 |
| 2 | 0.2113 | 0.214 | 0.0022 | 1.04 |
| 5 | 0.2021 | 0.2072 | 0.0051 | 2.52 |
| 20 | 0.2039 | 0.2095 | 0.0056 | 2.75 |
| 40 | 0.2043 | 0.2101 | 0.0058 | 2.84 |
| 60 | 0.2023 | 0.2088 | 0.0065 | 3.21 |

TABLE 7

TPU Lubrizol Pellethane ® 5863-87A Ch 14 - 25 mm Segments

| Dwell time (min) | Initial Mass (g) | final mass (g) | Change in mass (g) | Change in mass % |
|---|---|---|---|---|
| 0 | 0.2586 | 0.259 | 0.0000 | 0.00 |
| 2 | 0.2672 | 0.2804 | 0.0132 | 4.94 |
| 5 | 0.2537 | 0.2749 | 0.0212 | 8.36 |
| 20 | 0.2699 | 0.3063 | 0.0364 | 13.49 |
| 40 | 0.2738 | 0.3195 | 0.0457 | 16.69 |
| 60 | 0.2620 | 0.3161 | 0.0541 | 20.65 |

TABLE 8

TPU 85A Ch 14 - 25 mm Segments

| Dwell time (min) | Initial Mass (g) | final mass (g) | Change in mass (g) | Change in mass % |
|---|---|---|---|---|
| 0 | 0.2739 | 0.274 | 0.0000 | 0.00 |
| 2 | 0.2671 | 0.281 | 0.0140 | 5.24 |
| 5 | 0.2728 | 0.2940 | 0.0212 | 7.77 |
| 20 | 0.2724 | 0.3035 | 0.0311 | 11.42 |
| 40 | 0.2653 | 0.3026 | 0.0373 | 14.06 |
| 60 | 0.2748 | 0.3274 | 0.0526 | 19.14 |

Example 6

The effect that immersion time in a THF-MA/photo initiator mixture has on the critical buckling force of an anti-plasticized PVC tube was studied. In particular, plasticized PVC tubes (plasticized with TOTM) were immersed in a THF-MA/photo initiator mixture for different time periods prior to polymerizing the THF-MA absorbed into the tubes. More specifically, the proximal end portion (~15 cm) of PVC catheter tubes each having a length of 370 mm, a French size of Ch14 and a Shore hardness of 82 A were vertically dipped into a masking solution that included 10 wt % PVP K90 in 90 wt % Ethanol. The catheter tubes were then immersed in a mixture of 99 wt % of THF-MA and 1 wt % of Irgacure 2959. The tubes were immersed in the mixture at 22° C. for one of the following time periods—30 seconds, 60 seconds or 120 seconds. The tubes were then removed and rinsed in ethanol to remove any excess THF-MA/Irgacure mixture and the masks from the tubes' surfaces.

The catheter was then coated with a UV curable hydrophilic coating using the same base coat, top coat and process described above in Example 4. As also described above in Example 4, the THF-MA absorbed into the tube was polymerized during the hydrophilic coating process.

After the hydrophilic coating was applied and the THF-MA was polymerized, the critical buckling force of the tubes for each of the immersion times was measured using an Instron Tensile Tester with a 10N load cell and manual grips attached to the crosshead. The gauge length (clamp separation) of the Tester was set to 320 mm. The load cell was zeroed prior to mounting the tube sample. 3.1 mm Teflon rods of 3 cm length were placed into each end of the tube before mounting to the tester. The tube samples were then clamped so that the mandrel reinforced the segment of the tube in the grips preventing crushing of the tube lumen. The ratio of the stiffer section to softer section of catheter between the grips for each test was: 60:40 stiffer:softer. The clamped tubing was tensioned with 1N force so that the tube was straight and fully extended before starting the testing. During the testing, axial compressive loading was performed at a speed of 10 mm/sec. When the sample buckled, the test was ended and the critical buckling force was measured. The average Critical Buckling Force of a control catheter having a single durometer over the entire length was also measured. FIG. 1 is a picture showing one example of the testing set-up. Table 9 shows the average critical buckling force results of the tubes for each of the immersion time periods.

TABLE 9

| Time Period of Immersion in THF-MA/Irgacure (s) | Avg. Critical Buckling Force (N) |
|---|---|
| Control (Untreated) | 0.24 |
| 30 | 0.344 |
| 60 | 0.486 |
| 120 | 0.592 |

Example 7

The effect of the THF-MA/photo initiator mixture's temperature during immersion has on the critical buckling force of an anti-plasticized PVC tube was studied. In particular, plasticized PVC tubes (plasticized with TOTM) were immersed in THF-MA/photo initiator mixtures of different temperatures prior to polymerizing the THF-MA absorbed into the tubes. More specifically, the proximal end portion (~15 cm) of PVC catheter tubes each having a length of 370 mm, a French size of Ch14 and a Shore hardness of 82 A were vertically dipped into a masking solution that included 10 wt % PVP K90 in 90 wt % Ethanol. The catheter tubes were then immersed in a mixture of 99 wt % of THF-MA and 1 wt % of Irgacure 2959. The tubes were immersed in the THF-MA for 60 seconds at one of the following temperatures—12° C., 22° C. and 32° C. The tubes were then removed and rinsed in ethanol to remove any excess THF-MA/Irgacure mixture and the masks from the tubes' surfaces.

The tubes were then coated with a UV curable hydrophilic coating using the base coat, top coat and process described above in Example 4. As also described above in Example 4, the THF-MA absorbed into the tubes was polymerized during the hydrophilic coating process.

After the hydrophilic coating was applied and the THF-MA was polymerized, the critical buckling force of the tubes was measured using an Instron Tensile Tester and procedure described above in Example 6. The average Critical Buckling Force of a control catheter having a single durometer over the entire length was also measured. Table 10 shows the average results of the tubing for each of the immersion time periods.

TABLE 10

| Temperature (° C.) of Immersion in THF-MA/Irgacure for 60 seconds | Avg. Critical Buckling Force (N) |
|---|---|
| Control (Untreated) | 0.24 |
| 12° C. | 0.320 |
| 22° C. | 0.486 |
| 32° C. | 0.563 |

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A method of modifying a pre-formed polymeric tube of an intermittent urinary catheter by varying the flexibility along the length of the pre-formed polymeric tube, the pre-formed polymeric tube including a proximal end portion with an insertion tip and at least one eyelet and a distal end portion with a drainage member, the method comprising:
   contacting alternating sections along the length of the pre-formed polymeric tube of an intermittent urinary catheter with a polymerizable monomer, said polymerizable monomer being absorbed into the alternating sections along the length of the pre-formed polymeric tube; and
   polymerizing the polymerizable monomer absorbed in the alternating sections of the pre-formed polymeric tube, thereby increasing the stiffness of the alternating sections of the pre-formed polymeric tube and varying the flexibility along the length of the polymeric tube.

2. A method of making a pre-formed polymeric tube of an intermittent urinary catheter thereby varying the flexibility along the length of the polymeric tube, the catheter including a catheter tube having a proximal end portion with an insertion tip and at least one eyelet and a distal end portion with a drainage member, the method comprising:
   contacting a first non-inflatable section along the length of the pre-formed polymeric tube of an intermittent urinary catheter with a polymerizable monomer, said polymerizable monomer being absorbed into the first non-inflatable section of the pre-formed polymeric tube;
   contacting a second non-inflatable section along the length of the pre-formed polymeric tube, wherein the second non-inflatable section is spaced apart along the length of the pre-formed polymeric tube from the first non-inflatable section of the pre-formed polymeric tube; and
   polymerizing the polymerizable monomer absorbed in the first and second non-inflatable sections of the pre-formed polymeric tube, thereby increasing the stiffness of the first and second non-inflatable sections of the pre-formed polymeric tube and varying the flexibility along the length of the polymeric tube.

3. The method of claim 1, wherein the polymeric tube is non-radially expanding.

4. The method of claim 2, wherein the polymeric tube is non-radially expanding.

5. The method of claim 1 wherein the step of contacting comprises immersing the section of the polymeric tube in the polymerizable monomer.

6. The method of claim 1 wherein the step of contacting comprises contacting the section of the polymeric tube with a mixture comprising the polymerizable monomer and an initiator.

7. The method of claim 6 wherein the initiator is selected from the group of a photo-initiator, radiation-initiator, thermal-initiator or a redox-initiator.

8. The method of claim 6 wherein the initiator comprises a photoinitiator.

9. The method of claim 8 wherein the step of polymerizing comprises exposing the polymeric tube to UV light.

10. The method of claim 8 wherein prior to the polymerizing step, the method includes contacting an outer surface of the polymeric tube with a hydrophilic polymer; and
    the polymerizing step comprises exposing the polymeric tube to UV light to polymerize the monomer and crosslink the hydrophilic polymer to form a hydrophilic coating on the outer surface of the polymeric tube.

11. The method of claim 1 further including forming a hydrophilic coating on an outer surface of the polymeric tube.

12. The method of claim 1 wherein the polymerizable monomer comprises one or more of limonene, vinyl ethers and acrylates.

13. The method of claim 1 wherein the polymerizable monomer comprises one or more of Tricyclo[$5.2.1.0^{2,6}$] decanedimethanol diacrylate, Limonene, Trimethylolpropane ethoxylate triacrylate, Trimethylolpropane trimethacrylate, Trimethylolpropane triacrylate, Neopentyl glycol propoxylate (1 PO/OH) diacrylate, 1,6-Hexanediol ethoxylate diacrylate, Hydroxypivalyl hydroxypivalate bis[6-(acryloyloxy)hexanoate], Tri(ethylene glycol) divinyl ether, Tetrahydrofurfuryl methacrylate, Tetrahydrofuran, Tetrahydrofurfuryl acrylate, and 2-Methyltetrahydrofuran.

14. The method of claim 1 wherein the section of the polymeric tube comprises a distal end portion of the polymeric tube.

15. The method of claim 1 wherein the method further includes prior to the contacting step, applying a mask to a second section of the polymeric tube such that the mask substantially prevents the polymerizable monomer from being absorbed into the second section of the polymeric tube.

16. The method of claim 15 wherein the second section comprises a proximal end portion of the polymeric tube.

17. The method of claim 15 wherein the method further includes applying a second mask to a third section of the polymeric tube.

18. The method of claim 17 wherein the third section of the polymeric tube is adjacent a distal end of the polymeric tube.

* * * * *